US006391885B1

(12) United States Patent
Piazza et al.

(10) Patent No.: US 6,391,885 B1
(45) Date of Patent: May 21, 2002

(54) METHOD OF TREATING A PATIENT HAVING PRECANCEROUS LESIONS WITH PHENYL CYCLOAMINO PYRIMIDINONE DERIVATIVES

(75) Inventors: Gary A. Piazza, Highlands Ranch, CO (US); Rifat Pamukcu, Spring House, PA (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/564,196

(22) Filed: May 4, 2000

Related U.S. Application Data

(62) Division of application No. 08/484,002, filed on Jun. 7, 1995, now Pat. No. 6,060,477.

(51) Int. Cl.[7] ............... A61K 31/505; A61K 31/50; A61K 31/495

(52) U.S. Cl. .................. 514/258; 514/247; 514/248; 514/249

(58) Field of Search .................. 514/258, 247, 514/248, 249

(56) References Cited

U.S. PATENT DOCUMENTS 4,950,680 A    8/1990   Taylor et al.

FOREIGN PATENT DOCUMENTS

WO    WO 95/19978    7/1995

*Primary Examiner*—Jerome D. Goldberg
(74) *Attorney, Agent, or Firm*—Robert W. Stevenson

(57) ABSTRACT

Derivatives of Phenyl Cycloamino Pyrimidinone are useful for the treatment of patients having precancerous lesions. These compounds are also useful to inhibit growth of neoplastic cells.

4 Claims, No Drawings

METHOD OF TREATING A PATIENT HAVING PRECANCEROUS LESIONS WITH PHENYL CYCLOAMINO PYRIMIDINONE DERIVATIVES

This application is a Divisional of prior U.S. application Ser. No. 08/484,002 filed Jun. 7, 1995 now U.S. Pat. No. 6,060,477 entitled "Method of Treating a Patient Having Precancerous Lesions with Phen Cycloamino Pyrimidinone Derivatives," which is incorporated herein by reference.

TECHNICAL FIELD

This invention relates to methods for treatment or prevention of precancerous lesions.

BACKGROUND OF THE INVENTION

Each year in the United States alone, untold numbers of people develop precancerous lesions. These lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds which prevent or induce the remission of existing precancerous or cancerous lesions or carcinomas would greatly reduce illness and death from cancer.

Approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e. the cases of so-called common sporadic polyps), polyp removal will be effective to reduce the risk of cancer. In a small percentage of cases (i.e. the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g. hundreds or more) of polyps— literally covering the colon in some cases—making safe removal of the polyps impossible short of surgical removal of the colon.

Because each polyp carriers with it the palpable risk of cancerous development, polyposis syndrome patients invariably develop cancer if left untreated. Surgical removal of the colon is the conventional treatment. Many of these patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because therapy is often not effective and has severe side effects. Cancer prevention is important for recovered cancer patients who retain a risk of cancer reoccurrence. Also, cancer prevention is important for people who have not yet had cancer, but have hereditary factors that place them at risk of developing cancer. With the development of new diagnostic screening technologies, it is possible to identify those with high risk factors, such as the potential for polyposis syndrome, who would greatly benefit from chemopreventive drugs. Therefore, finding such anti-cancer drugs that can be used for prolonged preventive use is of vital interest to many people.

One way to find such drugs is to screen thousands of compounds for the same biological activity found in known chemopreventive and chemotherapeutic drugs. Most such drugs are now believed to kill cancer cells by inducing apoptosis, or as sometimes referred to as "programmed cell death." Apoptosis naturally occurs in virtually all tissues of the body, and especially in self-renewing tissues such as bone marrow, gut, and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis plays a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long term use, or use in otherwise healthy individuals with precancerous lesions. These side effects, which are a result of the high levels of cytotoxicity of the drugs, include hair loss, weight loss, vomiting and bone marrow immune suppression. Therefore, there is a need to identify new drug candidates for therapy that do not have such serious side effects in humans.

SUMMARY OF THE INVENTION

This invention is a method of treating patients with precancerous lesions or neoplasms by administering a pharmacologically effective amount of a compound of Formula I below to a patient in need of such treatment. Such compositions are effective in modulating apoptosis, and eliminating and inhibiting precancerous lesions, and neoplastic cells.

DETAILED DESCRIPTION OF THE PRESENTLY PREFERRED EMBODIMENTS

As discussed above, this invention is a method of treating a patient with precancerous lesions or neoplasms by administering a pharmacologically effective amount of the phenyl cycloamino pyrimidinone derivative represented by the following formula (I), or the pharmacologically acceptable salt thereof;

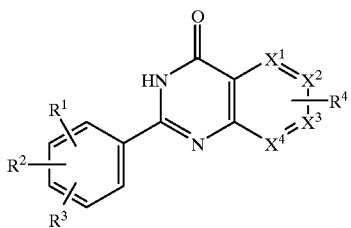

(I)

wherein $R^1$, $R^2$ and $R^3$ may be located at any of the available positions on the phenyl ring, each of $R^1$, $R^2$ and $R^3$ may be independently selected from hydrogen, halogen, a lower alkyl group, such as having 1 to 6 carbon atoms, a lower alkoxy, a lower alkenyl, a lower alkenoxy, a lower alkyl thio, a lower alkylamino, a di(lower)alkylamino, a cyano, an acylamino, a carboxyl, a carboalkoxy, a lower alkoxycarbonyl, a lower alkylcarbonyl a cyclo(lower)alkoxy and cyclo(lower)alkyl (lower)alkoxy in which the ring contains 3 to 8 carbon atoms, preferably 3–6 carbon atoms, a phenyl(lower) alkoxy a nitrogen containing ring, a lower alkylcarbamoyloxy, or a halogen substituted lower alkoxy group.

Further, $R^3$ may be —SO—NHR$^{12}$R$^{13}$, NO$_2$, NH$_2$, NHCOR$^{14}$, NHSO$_2$R$^{14}$ or N(SO$_2$R$^{14}$)$_2$; wherein $R^{12}$ and $R^{13}$ are each independently selected from H and $C_1$–$C_4$ alkyl optionally substituted with $CO_2R^5$, OH, pyridyl, 5-isoxazolin-3-onyl, morpholino or 1-imidazolidin-2-onyl; or together with the nitrogen atom to which they are attached form a pyrrolidino, piperidino, morpholino, 1-pyrazolyl or 4-(NR$^{15}$)-1-piperazinyl group wherein any of said groups may optionally be substituted with one or two substitutents selected from $C_1$–$C_4$ alkyl, $CO_2R^9$, NH$_2$ and OH; $R^{14}$ is $C_1$–$C_4$ alkyl or pyridyl; and $R^{15}$ is H, $C_1$–$C_4$ alkyl or (hydroxy)$C_2$–$C_3$ alkyl.

Preferably, $R^1$, $R^2$ and $R^3$ are independently a hydrogen, a halogen, a lower alkyl, a lower alkenyl, a lower alkoxy, a lower alkenyloxy, a phenyl(lower) alkoxy, a cyclo(lower) alkoxy. Preferably, $R^3$ is substituted at position 2 on the phenyl ring, in which case it is preferred that $R^1$ and $R^2$ are hydrogen. More preferably $R^3$ is lower alkoxy, lower alkenoxy, cyclopropylmethoxy or benzoxy. Most preferably $R^3$ is n-propyloxy.

$R^4$ may be a hydrogen, lower alkyl, a lower alkoxy, a phenyl, a hydroxy, a halogen, —NHCOR$^5$, —NHCONHR$^6$, 5-tetrazolyl, —CO$_2$R$^7$, a cyano, —CONR$^8$R$^9$, or —NR$^{10}$R$^{11}$, wherein $R^5$ to $R^9$ are independently hydrogen or lower alkyl or $R^9$ may be 5-tetrazolyl, and $R^{10}$ and $R^{11}$ are independently hydrogen or lower alkyl optionally substituted by hydroxy provided that the carbon atom adjacent to the nitrogen atom is not substituted by hydroxy.

Further, $R^4$ is $C_{1-6}$ alkylthio, $C_{1-6}$alkyl-sulphonyl, hydrazino, or —NR$^{10}$R$^{11}$, wherein $R^{10}$ and $R^{11}$ together with the nitrogen atom to which they are attached form a pyrrolidino, piperidino, hexahydroazepino, morpholino or piperazino ring, on $R^{10}$ and $R^{11}$ $C_{3-5}$cycloalkyl or $C_{1-6}$alkyl which is optionally substituted by —CF$_3$, phenyl, —S(O)$_n$C$_{1-6}$alkyl wherein n is 0, 1 or 2, —OR$^6$, —CO$_2$R$^7$ or —NR$^8$R$^9$ wherein $R^6$ to $R^9$ are independently hydrogen or $C_{1-6}$alkyl, provided that the carbon atom adjacent to the nitrogen atom is not substituted by said —S(O)$_n$C$_{1-6}$alkyl, —OR$^6$ or —NR$^8$R$^9$ groups.

Preferably, $R^4$ is a phenyl, a lower alkyl, a hydroxy, a lower alkoxy or —CONR$^8$R$^9$. Preferably, when $R^4$ is positioned on the pyrimidinone ring adjacent the oxygen, $R^4$ is —CONR$^8$R$^9$, in which case, it is preferred that $R^8$ is hydrogen and $R^9$ is 5-1H-tetrazolyl.

$X^1$, $X^2$, $X^3$ and $X^4$ may be independently nitrogen or carbon with the proviso that: at least one of $X^1$, $X^2$, $X^3$ and $X^4$ must be nitrogen and at least one of $X^1$, $X^2$, $X^3$ and X4 must be carbon; any two of $X^1$, $X^2$, $X^3$ and $X^4$ may be nitrogen; when $X^2$ and $X^4$ are nitrogen, $X^3$ must be carbon; and, when $X^1$ and $X^3$ are nitrogen, $X^2$ must be carbon.

A preferred group of compounds of formula (I) is that wherein $R^4$ is H, n-propyl, CN or CONH$_2$; $R^1$ is ethoxy; $R^2$ is hydrogen; $R^3$ is SO$_2$NR$^{12}$R$^{13}$, NO$_2$, NH$_2$, NHCOCH(CH$_3$)$_2$, NHSO$_2$CH(CH$_3$)$_2$, NHSO$_2$(3-pyridyl)]$_2$; $R^{12}$ is H, methyl or 2-hydroxyethyl; $R^{13}$ is methyl optionally substituted with 2-pyridyl or 5-isoxazolin-3-onyl, or ethyl 2-substituted with OH, CO$_2$CH$_2$CH$_3$, morpholino or 1-imidazolidin-2-onyl, or $R^{12}$ and $R^{13}$ together with the nitrogen atom to which they are attached form a (4- CO$_2$R$^5$) piperidino, 5-amino-3-hydroxy-1-pyrazolyl or 4-(NR$^{15}$)-1-piperazinyl group; $R^5$ is H or ethyl; $R^{15}$ is H, methyl or 2-hydroxyethyl; and $X^1$ is nitrogen. More preferably, $R^1$ is at position 2 and $R^3$ is at position 5 on the phenyl ring.

A particularly preferred group of compounds of formula (I) is that wherein $R^4$ is n-propyl or CN; $R^1$ is ethoxy; $R^2$ is hydrogen; $R^3$ is SO$_2$NR$^{12}$R$^{13}$, NHSO$_2$CH(CH$_3$)$_2$ , NHSO$_2$ (3-pyridyl) or N[SO$_2$(3-pyridyl)]$_2$; $R^{12}$ is H or methyl; $R^{13}$ is methyl, or ethyl 2-substituted with CO$_2$CH$_2$CH$_3$, morpholino or 1-imidazolidin-2-onyl, or $R^{12}$ and $R^{13}$ together with the nitrogen atom to which they are attached form a (4-CO$_2$R$^3$)piperidino or 4-(NR$^{15}$)-1-piperazinyl group; $R^5$ is H or ethyl; and $R^{15}$ is H, methyl or 2-hydroxyethyl.

"Alkyl group" refers to straight or branched chain $C_1$–$C_{12}$ groups such as methyl, ethyl, propyl, iso-propyl, n-butyl, t-butyl and amyl. "Alkoxy group" refers to hydroxy-substituted alkyl groups such as methoxy, ethoxy, propoxy, butoxy and amyloxy. "Alkoxycarbonyl group" refers to carbonyl-substituted alkoxy groups such as methoxycarbonyl, ethoxycarbonyl, propoxycarbonyl, butoxycarbonyl, amyloxycarbonyl, etc. "Alkylcarbonyl group" refers to carbonyl-substituted alkyl groups such as acetyl, propionyl, butyryl or others. "Halogen" refers to fluorine, chlorine, bromine and iodine. "Lower" refers to 6 or less carbon atoms.

The pharmacologically acceptable salt includes inorganic acid salts such as hydrochloride, hydrobromide, sulfate and phosphate; organic acid salts such as acetate, maleate, tartrate, methanesulfonate, benzenesulfonate and toluene-sulfonate; and amino acid salts such as argininate, aspartate and glutamate. Further, some of the compounds may form metal salts such as Na, K, Ca or Mg, and the pharmacologically acceptable salt of formula (I) also includes these metal salts.

Although the compound of formula I may be present as various isomers including geometrical isomers, i.e., cis-isomer and trans-isomer. and optical isomers, i.e., d-isomer and l-isomer depending upon the kinds and combination of the substituents, it is needless to say that the compounds include all of the isomers.

As used herein, the term "precancerous lesion" refers to lesions that exhibit histologic changes which are associated with an increased risk of cancer development. Examples include adenomatous polyps of the colon, dysplastic nevi of the skin and atypical hyperplasia of the breasts. Certain syndromes that commonly display precancerous lesions are also referred to by the term "precancerous" including dysplastic nevus syndrome and the colonic polyposis syndromes. "Precancerous" refers to these lesions or syndromes of various tissues whether or not the lesions are clinically identifiable.

As used herein, the term "carcinomas" refers to lesions which are cancerous. Examples include malignant melanomas, breast cancer, and colon cancer.

As used herein, the term, "neoplasm" refers to both precancerous and cancerous lesions.

As used herein, the term "halo" or "halogen" refers to chloro, bromo, fluoro and iodo groups, and the term "alkyl" refers to straight, branched or cyclic alkyl groups.

Compounds of formula I may be formulated into compositions together with pharmaceutically acceptable carriers for injection, oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories which may contain, in addition to the compounds of Formula I, excipients such as cocoa butter or a suppository wax.

The pharmaceutically acceptable carrier and compounds of Formula I are formulated into unit dosage forms for administration to a patient. The dosage levels of active ingredient (i.e. compounds of Formula I) in the unit dosage may be varied so as to obtain an amount of active ingredient effective to achieve polyp-eliminating activity in accordance with the desired method of administration (i.e. oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g. two to four times per day.

In another form, the invention is a method of inhibiting the growth of neoplastic cells by exposing them to an effective amount of the compound of formula [I] above.

In still another form, the invention is a method of inducing apoptosis in human cells by exposing those cells to an effective amount of the compound of formula [I] above where such cells are sensitive to this compound.

Additionally, in yet another form, the invention is a method of treating a patient having a disease which would benefit from regulation of apoptosis by treating the patient with an effective amount of the compound of formula [I] above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

The foregoing may be better understood from the following examples, which are presented for purposes of illustration and are not intended to limit the scope of the invention. As used in the following examples, the references to substituents such as R, $R^1$, $R^2$ etc., refer to the corresponding compounds and substituents in the Formula above.

Preferable specific examples of the compound will now be described in order to facilitate the understanding of the present invention, though it is needless to say that the compounds of the present invention are not limited to these examples.

EXAMPLE 1

2-[2-Ethoxy-5-(2-morpholinoethylsulphamoyl) phenyl]-8-n-propylpyridor[3,2-d]pyrimidin-4(3H)-one 2-(2-Ethoxyphenyl)-8-n-propylpyrido[3,2-d]pyrimidin-4(3H)-one (Preparation 8; 1.09 g, 0.00353 mol) was added portion-wise to stirred chlorosulphonic acid (4 ml) under a nitrogen atmosphere at 0° C. The mixture was stirred at ambient temperature for 18 hours and then added cautiously to ice/water (100 g). The resulting white precipitate was collected by filtration, washed with 2-propanol and then with diethyl ether, and used without further purification.

The crude sulphonyl chloride (0.16 g, 0.0004 mol) was added to a stirred solution of 4-(2-aminoethyl)-morpholine (0.156 g, 0.0012 mol) in ethanol (40 ml), and the resulting solution stirred at ambient temperature for 18 hours. The solvent was evaporated under vacuum, the residue suspended in saturated aqueous sodium carbonate solution (20 ml) and this mixture extracted with dichloromethane (3×20 ml). The organic extracts were combined, dried ($Na_2SO_4$) and evaporated under vacuum, and the resulting residue chromatographed on silica gel (4 g) using a methanol in dichloromethane elution gradient (0–5% methanol). Trituration of the product with diethyl ether gave the title compound as an off-white solid (0.05 g, 25%), m.p. 165–166° C.

The following seven compounds were obtained from the same sulphonyl chloride and the appropriate amine by procedures similar to that described in Example 1.

EXAMPLE 2

2-[2-Ethoxy-5(4-methyl-1-piperazinylsulphonyl) phenyl]-8-n-propylpyrido[3,2d]pyrimidin-4(3H)-one Obtained using 1-methylpiperazine in 70% yield, m.p. 211–212° C.

EXAMPLE 3

2-[2-Ethoxy-5-(1-piperazinylsulphonyl)phenyl]-8-n-propylpyrido[3,2-d]pyrimidin-4(3H)-one Obtained using piperazine in 43% yield, m.p. 178–180° C.

EXAMPLE 4

2-[2-Ethoxy-5-(4-ethoxycarbonylpiperidinosulphonyl)phenyl]-8-n-propylpyrido[3,2-d]pyrimidin-4(3H)-one Obtained using ethyl isonipecotate in 86% yield, m.p. 204–205° C.

EXAMPLE 5

2-[2-Ethoxy-5-(N-2-ethoxycarbonylethyl-N-methyl-sulphamoyl)phenyl]-8-n-propylpyrido[3,2-d] pyrimidin-(3H)-one Obtained using ethyl 3-(methylamino)propionate in 67% yield, m.p. 145–146° C.

EXAMPLE 6

2-[2-Ethoxy-5-(methylsulphamoyl)phenyl]-8-n-propylpyrido[3,2-d]pyrimidin-4(3H)-one Obtained using methylamine (in ethanol solution) in 58% yield, m.p. 216–219° C.

EXAMPLE 7

2-{2-Ethoxy-5-[4-(2-hydroxyethyl)-1-piperazinylsulphonyl]phenyl}-8-n-propylpyridor[3,2-d]pyrimidin-4(3H)-one Obtained using 1-(2-hydroxyethyl)piperazine in 34% yield, m.p. 187–188° C.

EXAMPLE 8

2-{2-Ethoxy-5-[2-(1-imidazolidin-2-onyl) ethylsulphamoyl)phenyl}-8-n-propylpyrido[3,2-d] pyrimidin-4-(3H)-one Obtained using 1-(2-aminoethyl)imidazolidin-2-one in 44% yield, m.p. 221–222° C.

EXAMPLE 9

2-[5-(4-Carboxypiperidinosulphonyl)-2-ethoxyphenyl]-8-n-propylpyrido[3,2-d]pyrimidin-4(3H)-one A mixture of 2-[2-ethoxy-5-(4-ethoxycarbonylpiperidinosulphonyl)phenyl]-8-n-propylpyrido[3,2-d]pyrimidin-4(3H)-one (Example 4; 0.55 g, 0.001 mol), potassium hydroxide (0.146 g, 0.0026 mol) and ethanol (35 ml) was stirred under reflux for 5 hours, then allowed to cool. The solvent was evaporated under vacuum, and the residue chromatographed twice on ion-exchange resin (Bio-rad AG50W-X8 $H^+$, 27.5 g) using a pyridine in water elution gradient (2–50% pyridine). Crystallization of the product from aqueous ethanol gave the title compound as a colourless solid (0.09 g, 8%), m.p. 262–264° C.

EXAMPLE 10

2-(2-Ethoxy-5-nitrophenyl)-8-n-propylpyrido[3,2-d] pyrimidin-4(3H)-one

A solution of 2-(2-ethoxyphenyl)-8-n-propylpyrido-(3,2-d]pyrimidin-4(3H)-one (Preparation 8; 0.80 g, 0.0026 mol) in a mixture of concentrated sulphuric acid (5.4 ml) and concentrated nitric acid (0.20 ml) was stirred at ambient temperature for 4.5 hours. The mixture was then poured cautiously into stirred ice/water (50 g) and the resulting mixture extracted with a methanol:dichloromethane mixture (1:9, 3×50 ml). The organic extracts were combined, dried ($MgSO_4$) and evaporated under vacuum, and the residue crystallized from ethyl acetate:methanol to give the title compound as an off-white solid (0.71 g, 77%), m.p. 257–259° C.

EXAMPLE 11

2-(5-Amino-2-ethoxyphenyl)-8-n-propylpyrido[3,2-d]pyrimidin-4(3H)-one

Stannous chloride dihydrate (2.48 g, 0.011 mol) was added to a stirred solution of 2-(2-ethoxy-5-nitrophenyl)-8-n-propylpyrido[3,2-d)pyrimidin-4(3H)-one (Example 10; 0.78 g, 0.0022 mol) in ethanol (10 ml) and the mixture was heated under reflux for 2 hours, allowed to cool, basified to pH 11 by the addition of 10% aqueous sodium hydroxide solution, and then extracted with methanol:dichloromethane (1:9, 3×50 ml). The organic extracts were combined, dried ($MgSO_4$) and evaporated under vacuum, then the residue was chromatographed on silica gel (12 g) using a methanol in dichloromethane elution gradient (0–2% methanol). Trituration of the product with hexane:ethyl acetate gave the title compound as a colourless solid (0.51 g, 71%), m.p. 156–158° C.

EXAMPLES 12 & 12A

2-{2-Ethoxy-5-[(bis-3-pyridylsulphonyl)amino] phenyl}-8-n-propylpyrido[3,2-d]pyrimidin-4(3H)-one and 2-[2-Ethoxy-5-(3-pyridylsulphonylamino) phenyl]-8-n-propylpyrido[3,2-d]pyrimidin-4(3H)-one 3-Pyridylsulphonyl chloride (0.201 g, 0.00113 mol) was added to a stirred mixture of 2-(5-amino-2-ethoxyphenyl)-8-n-propylpyrido[3,2-d]pyrimidin-4(3H)-one (Example 11; 0.25 g, 0.00077 mol) and pyridine (5 ml), and the resulting mixture stirred at ambient temperature for 12 days and then added to water (50 ml). The resulting solution was acidified to pH 1 with 2N hydrochloric acid, and then extracted with methanol:dichloromethane (1:9, 3×50 ml). The combined extracts were dried (MgSO₄) and evaporated under vacuum and the residue chromatographed on silica gel (12 g) using a methanol in dichloromethane elution gradient (0–2% methanol). Crystallization of the product from ethyl acetate:methanol gave the first title compound as an off-white solid (0.123 g, 34%), m.p. 242–243° C.

The aqueous phase was extracted further with methanol-dichloromethane (1:9, 3×50 ml), and the combined extracts dried (MgSO₄) and evaporated under vacuum. Chromatography of the residue on silica gel (12 g), using a methanol in dichloromethane elution gradient (2–5% methanol), followed by crystallization of the product from ethyl acetate:methanol, gave the second title compound as a white solid (0.104 g, 29%), m.p. 229–231° C.

EXAMPLE 13

2-[2-Ethoxy-5-(2-propylsulphonylamino)phenyl]-8-n-propyl-pyrido[3,2-d]pyrimidin-4(3H)-one The title compound was prepared using 2-propylsulphonyl chloride following the procedure of Example 12 and was obtained as a white solid (55%), m.p. 207–210° C.

EXAMPLE 14

2-[2-Ethoxy-5-(4-methyl-1-piperazinylsulphonyl) phenyl]pyrido[3,2-d]pyrimidin-4(3H)-one 2-(2-Ethoxyphenyl)pyrido[3,2-d]pyrimidin-4(3H)-one (Preparation 10; 1.2 g, 0.0045 mol) was added portion-wise to stirred chlorosulphanic acid (6 ml) under a nitrogen atmosphere at 0° C. The mixture was stirred at ambient temperature for 18 hours and then added cautiously to ice/water (100 g). The resulting solution was brought to pH 5 by the addition of saturated aqueous sodium carbonate solution and then extracted with dichloromethane methanol (9:1, 3×150 ml). The organic fractions were combined, dried (MgSO₄) and evaporated under vacuum to give the sulphonyl chloride, which was used without further purification.

The crude sulphonyl chloride (0.55 g, 0.0015 mol) was added to a stirred solution of 1-methylpiperazine (0.45 g, 0.0045 mol) in ethanol (10 ml), and the resulting solution stirred at ambient temperature for 18 hours. The solvent was evaporated under vacuum and the residue chromatographed on silica gel (10 g), eluting with a mixture of dichloromethane:methanol:0.880 aqueous ammonia solution (95:5:1). Crystallization of the product from ethyl acetate:methanol gave the title compound as a white solid (0.325 g, 51%), m.p. 212–215+ C.

The following four compounds were obtained from the same sulphonyl chloride and the appropriate amine by procedures similar to that described in Example 14.

EXAMPLE 15

2-{2-Ethoxy-5[(bis-2-hydroxyethyl)sulphamoyl] phenyl}pyrido[3 2-d]pyrimidin-4(3H)-one Obtained using diethanolamine in 37% yield, m.p. 223–225° C.

EXAMPLE 16

2-{2-Ethoxy-5-[(2-pyridylmethyl)sulphamoyl] phenyl}pyrido[3,2-d]pyrimidin-4(3H)-one Obtained using 2-aminomethylpyridine in 50% yield, m.p. 230–231° C.

EXAMPLE 17

2-{2-Ethoxy-5-[(5-isoxazolin-3-onylmethyl) sulphamoyl]phenyl}pyrido[3,2-d]pyrimidin-4(3H)-one Obtained using muscimol hydrate in 32% yield, m.p. indeterminate (amorphous solid). Rf 0.40 (dichloromethane:methanol:glacial acetic acid, 90:10:1).

EXAMPLE 18

2-[5-(5-Amino-3-hydroxy-1-pyrazolylsulphonyl)-2-ethoxyphenyl]pyrido[3,2-d]pyrimidin-4(3H)-one Obtained using 3-amino-5-hydroxypyrazole in 34% yield, m.p. 246–249° C.

EXAMPLE 19

2-(2-Ethoxy-5-nitrophenyl)pyrido(3,2-d]pyrimidin-4(3H)-one

A stirred solution of 2-(2-ethoxyphenyl)pyrido(3,2-d) pyrimidin-4(3H)-one (Preparation 10; 1.4 g, 0.0052 mol) in concentrated sulphuric acid (11 ml) at 0° C., was treated dropwise with concentrated nitric acid (0.4 ml). The reaction mixture was allowed to warm to ambient temperature, stirred for a further 18 hours, then added dropwise to ice/water (70 g). The resulting precipitate was collected by filtration, dried under vacuum and then crystallized from acetonitrile to give the title compound as a pale yellow solid (0.22 g, 86%), m.p. 251–254° C.

EXAMPLE 20

2-(5-Amino-2-ethoxyphenyl)pyrido[3,2-d] pyrimidin-4(3H)-one

A stirred mixture of 2-(2-ethoxy-5-nitrophenyl)pyrido(3, 2-d]pyrimidin-4(3H)-one (Example 19; 1.1 g, 0.00353 mol), stannous chloride dihydrate (4.0 g, 0.0177 mol) and ethanol (15 ml) was heated under reflux for 4 hours. The resulting mixture was allowed to cool, diluted with water (15 ml), adjusted to pH 8 with 2N aqueous sodium hydroxide solution, vigorously shaken with dichloromethane (30 ml), and then this mixture filtered. The aqueous phase was separated and extracted further with dichloromethane (2×30 ml), and the organic extracts were then combined, dried (MgSO₄) and evaporated under vacuum. Crystallization of the product from acetonitrile gave the title compound as a hydrated yellow solid (0.72 g, 72%), m.p. 208–210° C.

EXAMPLE 21

2-[Ethoxy-5-(2-propylsulphonylamino)phenyl] pyrido[3,2-d]pyrimidin-4(3H)-one

The title compound was prepared using 2-propylsulphonyl chloride and 2-(5-amino-2-ethoxyphenyl)pyrido[3,2-d]pyrimidin-4(3H)-one (Example 20), following the procedure of Example 12, and was obtained as a hydrated solid (59%), m.p. 211–213° C.

EXAMPLE 22

2-(5-Isobutyrylamino-2-ethoxyphenyl)pyrido[3,2-d] pyrimidin-4(3H)-one

The title compound was prepared using isobutyryl chloride and 2-(5-amino-2-ethoxyphenyl)pyrido[3,2-d]

pyrimidin-4(3H)-one (Example 20), following the procedure of Example 12, and was obtained as a white solid (80%), m.p. 256–259° C.

EXAMPLE 23

8-Cyano-2-[2-ethoxy-5-(1-piperazinylsulphonyl) phenyl]pyrido[3,2-d]pyrimidin-4(3H)-one The title compound was prepared from 8-cyano-2-(2-ethoxyphenyl)pyrido[3,2-d]pyrimidin-4(3H)-one (Preparation 14) and piperazine, following the procedure of Example 1, and was obtained as an off-white solid (22%), m.p. 172–175° C.

EXAMPLE 24

8-Cyano-2-[2-ethoxy-5-(4-methyl-1-piperazinylsulphonyl)phenyl]pyrido[3,2-d]pyrimidin-4(3H)-one The title compound was prepared from 8-cyano-2-(2-ethoxyphenyl)pyrido[3,2-d]pyrimidin-4(3H)-one (Preparation 14) and 1-methylpiperazine, following the procedure of Example 1, and was obtained as an off-white solid (8%), m.p. 239–240° C.

EXAMPLE 25

8-Carbamoyl-2-[2-ethoxy-5-(4-methyl-1-piperazinylsulphonyl)phenyl]pyrido[3,2-d]pyrimidin-4(3H)-one The title compound was prepared from 8-carbamoyl-2-(2-ethoxyphenyl)pyrido(3,2-d]pyrimidin-4(3H)-one (Preparation 16) and 1-methylpiperazine, following the procedure of EXAMPLE 1, and was obtained as a solvated white powder (13%), m.p. 237–238° C.

EXAMPLE 26

7-Methylthio-4-oxo-2-(2-propoxyphenyl)-3,4-dihydropyrimido[4,5-d]pyrimidine

2-Propoxybenzamidine (from sodium, 0.3 g, in ethanol, 50 ml, and 2-propoxybenzamidine hydrochloride, 2.77 g) was dissolved in 2-propanol (20 ml) and the resulting cooled (2° C.) solution was added to a cooled (2° C.) solution of ethyl 4-chloro-2-methylthio-5-pyrimidine carboxylate (2 g) in 2-propanol (30 ml). The reaction mixture was stirred at 2° C. for 2 hours and was then left overnight at ambient temperature to yield a white crude product, 1.18 g, m.p. 179–181° C. Recrystallization from ethanol yielded the title compound, 0.92 g, m.p. 186–187° C.

EXAMPLE 27

7-Methylthio-2-(2-ethoxyphonyl)-4-oxo-3,4-dihydropyrimido[4,5-d]pyrimidine

2-Ethoxybenzamidine (from sodium, 0.08 g, in ethanol, 10 ml, and 2-ethoxybenzamidine hydrochloride, 0.70 g) was dissolved in acetonitrile (10 ml) and the resulting cooled (2° C.) solution was added to a cooled (2° C.) suspension of ethyl 4-chloro-2-methylthio-5-pyrimidine carboxylate (0.81 g) in acetonitrile (10 ml). The reaction mixture was stirred at 2° C. for one hour. Triethylamine (0.35 g) was added and the reaction mixture was stirred at ambient temperature for 21 hours to yield a white precipitate, 0.22 g, which was collected by filtration. The filtrate was reduced in volume under reduced pressure to yield a second crop of solid. 0.41 g. The products were combined and recrystallized from ethanol to yield the title compound, 0.30 g, m.p. 224.5–225.5° C.

EXAMPLE 28

7-Methylthio-2-(2-methoxyphenyl)-4-oxo-3,4-diydropyrimido[4, 5-d]pyrimidine

2-Methoxybenzamidine (from sodium. 0.15 g, in ethanol, 20 ml, and 2-methoxybenzamidine methanesulphonate, 1.70 g) was dissolved in acetonitrile (20 ml) and the resulting cooled (2° C.) solution was added to a cooled (2° C.) suspension of ethyl 4-chloro-2-methylthio-5-pyrimidine carboxylate (2.33 g) in acetonitrile (20 ml). Triethylamine (0.66 g) was added and the reaction mixture was stirred at 2° C. for one hour and at ambient temperature for 18 hours. Acetonitrile was removed under reduced pressure and water (25 ml) was added. The mixture was cooled and a white solid was collected, washed with water and recrystallized from ethanol to yield the title compound, 0.46 g, m.p. 229–231° C. (dec.).

EXAMPLE 29

7-Methylthio-2-(2-Isobutoxyphenyl)-4-oxo-3,4-diydropyrimido[4,5-d]-pyrimidine

Ethyl 4-chloro-2-methylthio-5-pyrimidine carboxylate (1.50 g) followed by triethylamine (0.65 g) was added to a stirred mixture of 2-isobutoxybenzamidine hydrochloride (1.46 g) and triethylamine (0.65 g) in acetonitrile (150 ml). The reaction mixture was stirred at 5° C. for 15 minutes and then at ambient temperature for 3 days. A solid (0.55 g) was collected by filtration and the filtrate was reduced in volume to yield a second crop of solid (0.47 g). The solids were combined and recrystallized from ethanol to yield the title compound, 0.57 g, m.p. 185–186° C.

EXAMPLE 30

7-Methylthio-2-(2-cyclopropylmethoxyphenyl)-4-oxo-3,4-dihydropyrimido[4,5-d]pyrimidine In a similar manner to Example 29 reaction of ethyl 4-chloro-2-methylthio-5-pyrimidine carboxylate (1.50 g) with 2-cyclopropylmethoxybenzamidine hydrochloride (1.45 g) and triethylamine (1.30 g) in acetonitrile (50 ml) yielded a white solid (1.18 g) which was collected, dissolved in chloroform and the chloroform solution was extracted twice with 2 Normal hydrochloric acid. The chloroform solution was evaporated under reduced pressure and the residue was recrystallized from ethanol to yield the title compound, 0.52 g, m.p. 186–187° C.

EXAMPLE 31

7-Methylthio-2-(2-allyloxyphenyl)-4-oxo-3,4-dihydropyrimido[4,5-d]pyrimidine

2-Allyloxybenzamidine (from sodium, 0.22 g, in ethanol, 100 ml, and 2-allyloxybenzamidine hydrochloride, 2.00 g) was dissolved in acetonitrile (50 ml) and the resulting cooled (2° C.) solution was added to a cooled (2° C.) solution of ethyl 4-chloro-2-methylthio-5-pyrimidine carboxylate (2.19 g) in acetonitrile (50 ml). The temperature was allowed to rise and the reaction mixture was stirred overnight at ambient temperature. The volume of the reaction mixture was reduced by evaporation under reduced pressure to yield a solid (0.96 g) which was collected. More product (0.45 g) precipitated from the filtrate. The combined products were recrystallized twice from ethanol to yield the title compound, 340 mg, m.p. 205–206° C.

EXAMPLE 32

7-Amino-4-oxo-2-(2-propoxyphenyl)-3,4-dihydropyrimido[4,5-d]pyrimidine

7-Methylthio-4-oxo-2-(2-propoxyphenyl)-3,4-dihydropyrimido[4,5-d]pyrimidine (1.55 g) was heated in ethanolic ammonia (50 ml) in a pressure vessel for 8 hours at 90° C. and then for 8 hours at 145° C. After cooling a grey solid (0.64 g) was collected and was recrystallized from ethanol (with charcoal) to yield a crude product (0.47 g) which was recrystallized from ethanol to yield the title compound, 0.29 g, m.p. 261–262° C.

EXAMPLE 33

7-Methylamino-4-oxo-2-(2-propoxyphenyl)-3,4-dihydropyrimido[4,5-d]pyrimidine

7-Methylthio-4-oxo-2-(2-propoxyphenyl)-3,4-dihydropyrimido[4,5-d]pyrimidine (1.40 g) was treated with a solution of methylamine in industrial methylated spirit (33%; 30 ml) in a pressure vessel for 9 hours at 90° C. The reaction mixture was evaporated under reduced pressure to yield a cream solid which was dissolved in chloroform. The organic solution was washed with water, dried (magnesium sulphate) and evaporated under reduced pressure to yield a cream solid. Elution from silica with chloroform:methanol (25:1) yielded a crude product which was recrystallized twice from ethanol to yield the title compound, 0.31 g, m.p. 235–236° C.

EXAMPLE 34

7-Dimethylamino-4-oxo-2-(2propoxyphenyl)-3,4 dihydropyrimido[4,5-d]pyrimidine

7-Methylthio-4-oxo-2-(2-propoxyphenyl)-3,4-dihydropyrimido[4,5-d]pyrimidine (0.60 g) was treated with a solution of dimethylamine in industrial methylated spirit (33%; 20 ml) in a pressure vessel for 18 hours at 90° C. The cooled reaction mixture was evaporated under reduced pressure to yield a solid which was dissolved in aqueous sodium hydroxide. The filtered aqueous solution was neutralized with a few drops of concentrated hydrochloric acid to yield a pale yellow solid which was recrystallized from 2-propanol to yield the title compound, 0.33 g, m.p. 177.5–178.5° C.

EXAMPLE 35

7-Hydrazino-4-oxo-2-(2-propoxyphenyl)-3,4-dihydropyrimido[4,5-d]pyrimidine

A stirred mixture of 7-methylthio-4-oxo-2-(2-propoxyphenyl)-3,4-dihydropyrimido[4,5-d]pyrimidine (1.31 g) and hydrazine hydrate (3 ml) in ethanol (30 ml) was heated under reflux for 3 hours to yield a yellow precipitate. The reaction mixture was cooled overnight and the yellow precipitate was collected and washed with ethanol and water to yield the title compound, 0.80 g, m.p. 219–220° C.

EXAMPLE 36

4-Oxo-2-(2-propoxyphenyl) 3,4-dihydropyrimido[4,5-d]pyrimidine

A mixture of 7-hydrazino-4-oxo-2-(2-hydropoxyphenyl)-3,4-dihydropyrimido[4,5-d]pyrimidine (0.40 g) and silver oxide (0.32 g) in methanol (40 ml) was stirred at ambient temperature for 18 hours and at 45–50° C. for 24 hours. The cooled reaction mixture was evaporated under reduced pressure and the residue was eluted from a silica column with chloroform. The combined fractions containing product were evaporated under reduced pressure to yield a white solid which together with another sample (27 mg), similarly prepared, was recrystallized from 2-propanol to yield the title compound, 136 mg, m.p. 142–143° C.

EXAMPLE 37

7-Ethylamino-4-oxo-2-(2-propoxyphenyl) 3,4-dihydropyrimido[4,5-d]pyrimidine

In a similar manner to Example 9 reaction of 7-methylthio-4-oxo-2-(2-propoxyphenyl)-3-4-dihydropyrimido[4,5-d]pyrimidine (0.60 g) and 33% ethylamine in ethanol (20 ml) yielded the title compound, 0.29 g, m.p. 181–182° C. (recrystallized from ethanol/water and then from ethanol).

EXAMPLE 38

7-(2-Hydroxyethylamino)-4-oxo 2-(2-propoxyphenyl)-3,4-dihydropyrimido[4,5-d] pyrimidine A stirred mixture of 7-methylthio-4-oxo-2-(2-propoxyphenyl)-3,4-dihydropyrimido[4,5-d]pyrimidine (0.60 g) and ethanolamine (0.25 ml) in ethanol (20 ml) was heated under reflux for 19 hours. More ethanolamine (0.75 ml) was added and stirring under reflux continued for 16 hours. A white crystalline solid which precipitated from the cooled reaction mixture was collected, washed with cold ethanol and recrystallized from ethanol to yield the title compound, 0.38 g, m.p. 204–205.5° C.

EXAMPLE 39

7-Ethyl-4-oxo-2-(2-propoxyphenyl)-3,4-dihydropyrimido[4,5-d]pyrimidine

In a similar manner to Example 28 reaction of ethyl 4-chloro-2-ethyl-5-pyrimidine carboxylate (0.86 g) with 2-propoxybenzamidine (from sodium, 0.1 g, in ethanol, 10 ml, and 2-propoxybenzamidine methanesulphonate, 1.20 g) and triethylamine (0.4 g) in acetonitrile (25 ml) for 3 days at ambient temperature yielded a crude product, which was recrystallized twice from 2-propanol-ether to yield the title compound, 95 mg, m.p. 118–119° C.

EXAMPLE 40

7-Methylamino-2-(2-methoxyphenyl)-4-oxo-3,4-dihydropyrimido[4,5-d]pyrimidine

In a similar manner to Example 33 reaction of 7-methylthio-2-(2-methoxyphenyl)-4-oxo-3,4-dihydropyrimido[4,5-d]pyrimidine (0.75 g) and 33% methylamine in industrial methylated spirit (25 ml) for 18 hours yielded the title compound, 0.38 g, m.p. 265–267° C. (recrystallized twice from methanol).

EXAMPLE 41

7-Phenyl-4-oxo-2-(2-propoxyphenyl)-3,4-dihydropyrimido[4,5-d]pyrimidine

In a similar manner to Example 28 reaction of ethyl 4-chloro-2-phenyl-5-pyrimidine carboxylate (1.05 g) with 2-propoxybenzamidine (from sodium, 0.10 g, in ethanol, 10 ml, and 2-propoxybenzamidine methanesulphonate, 1.20 g) and triethylamine (0.40 g) in acetonitrile (25 ml) for 3 days at ambient temperature yielded a crude product which was recrystallized from methanol to yield the title compound, 0.52 g, m.p. 203–4° C.

EXAMPLE 42

7-Morpholino-4-oxo-2-(2-propoxyphenyl)-3,4-dihydropyrimido[4,5-d]pyrimidine

A stirred solution of 7-methylthio-4-oxo-2-(2-propoxyphenyl)-3,4-dihydropyrimido[4,5-d]pyrimidine (0.60 g) and morpholine (1.25 g) in pyridine (20 ml) was heated under reflux for 45 hours. The reaction mixture was evaporated under reduced pressure to yield a crude product which was washed with water and twice recrystallized from methanol to yield the title compound, 0.25 g., m.p. 175.5–177° C.

EXAMPLE 43

7-Cyclopropylamino-4-oxo-2-(2-propoxyphenyl)-3,4-dihydropyrimido[4,5-d]pyrimidine A stirred mixture of 7-methylthio-4-oxo-2-(2-propoxyphenyl)-3,4-dihydropyrimido[4,5-d]pyrimidine (0.60 g) and cyclopropylamine (1.2 ml) in ethanol (20 ml) was heated for 18 hours at 90° C. in a pressure vessel. Further cyclopropylamine (1 ml) was added and the reaction mixture was stirred in a pressure vessel for 18 hours at 100° C. and then for 20 hours at 120° C. The cooled reaction mixture was evaporated under reduced pressure to yield a residue which was dissolved in 1 Normal sodium hydroxide. The resultant solution was treated with charcoal, filtered, and the filtrate neutralized by the addition of concentrated hydrochloric acid which caused the precipitation of a crude product. The crude product was eluted from a silica column with chloroform as eluant, and the combined fractions containing product were evaporated under reduced pressure to yield a residue. This was twice recrystallized from methanol to yield the title compound, 0.23 g, m.p. 207.5–208.5° C.

EXAMPLE 44

7-Acetamido-4-oxo-2-(2-propoxyphenyl)-3,4-dihydropyrimido[4,5-d]pyrimidine

A stirred mixture of 7-amino-4-oxo-2-(2-propoxyphenyl)-3,4-dihydropyrimido[4,5-d]pyrimidine (0.59 g) and acetic anhydride (5 ml) was heated under reflux for 1.5 hours. Excess acetic anhydride was removed under reduced pressure. The solid residue was washed with water and triturated with hot methanol to yield the title compound, 0.57 g, m.p. 273–4° C.

EXAMPLE 45

7-Propylamino-4-oxo-2-(2-propoxyphenyl)-3,4-dihydropyrimido[4,5-d]pyrimidine

In a similar manner to Example 34 reaction of 7-methylthio-4-oxo-2-(2-propoxyphenyl)-3,4-dihydropyrimido[4,5-d]pyrimidine (0.60 g) and n-propylamine (1.44 g) in ethanol (20 ml) yielded the title compound, 0.46 g, m.p. 185.7° C. (recrystallized from ethanol).

EXAMPLE 46

7-(3-Hydroxypropylamino)-4-oxo-2-(2-propoxyphenyl)-3,4-dihydropyrimido[4,5-d]pyrimidine In a similar manner to Example 38, reaction of 7-methylthio-4-oxo-2-(2-propoxyphenyl)-3,4-dihydropyrimido[4,5-d]pyrimidine (0.45 g) and 3-amino-1-propanol (0.98 g) in ethanol (15 ml) yielded the title compound, 0.31 g, m.p. 185–6° C. (recrystallized from ethanol).

EXAMPLE 47

7-(2-Methoxyethylamino)-4-oxo-2-(2-propoxyphenyl)-3,4-dihydropyrimido[4,5-d]pyrimidine In a similar manner to Example 38, reaction of 7-methylthio-4-oxo-2-(2-propoxyphenyl)-3,4-dihydropyrimido[4,5-d]pyrimidine (0.41 g) and methoxyethylamine (1.04 g) in ethanol (15 ml) for 48 hours yielded the title compound, 0.38 g. m.p. 193–4° C. (recrystallized twice from methanol).

EXAMPLE 48

7-(2-Dimethylaminoethylamino)-4-oxo-2-(2-propoxyphenyl)-3,4-dihydropyrimido[4,5-d]pyrimidine In a similar manner to Example 38, reaction of 7-methylthio-4-oxo-2-(2-propoxyphenyl)-3,4-dihydropyrimido[4,5-d]pyrimidine (0.49 g) and N,N-dimethylethylenediamine (1.24 g) in ethanol (20 ml) yielded the title compound, 0.46 g. m.p. 181–2° C. (recrystallized for methanol).

EXAMPLE 49

7-(2-Hydroxypropylamino)-4-oxo-2-(2-propoxyphenyl)-3,4-dihydropyrimido[4,5-d]pyrimidine In a similar manner to Example 38 reaction of 7-methylthio-4-oxo-2-(2-propoxyphenyl)-3,4-dihydropyrimido[4,5-d]pyrimidine (0.41 g) and 1-amino-2-propanol (0.97 g) in ethanol (15 ml) for 40 hours yielded the title compound 0.37 g, m.p. 212.5–214° C. (recrystallized from methanol).

EXAMPLE 50

7-(3-Methylthiopropylamino)-4-oxo-2-(2-propoxyphenyl)-3,4-dihydropyrimido[4,5-d]pyrimidine In a similar manner to Example 38 reaction of 7-methylthio-4-oxo-2-(2-propoxyphenyl)-3,4-dihydropyrimido[4,5-d]pyrimidine (0.79 g) and methylthiopropylamine (0.50 g) in ethanol (15 ml) for 40 hours yielded a crude product which was purified by elution from silica with 40–60° petroleum ether:chloroform (gradient elution) to yield the title compound 0.52 g, m.p. 173–4° C. (recrystallized from methanol).

EXAMPLE 51

7-(2-Aminoethylamino)-4-oxo-2-(2-propoxyphenyl)-3,4-dihydropyrimido[4,5-d]pyrimidine hydrochloride A stirred solution of 7-methylthio-4-oxo-2-(2-propoxyphenyl)-3,4-dihydropyrimido[4,5-d]pyrimidine (0.49 g) and ethylenediamine (0.90 g) in ethanol (15 ml) was heated under reflux for 21 hours. Ethanol was removed under reduced pressure and the residue was dissolved in 1

Normal hydrochloric acid. The acidic solution was extracted with chloroform (3×10 ml), neutralized (to pH 6–7) with 2 Normal sodium hydroxide and evaporated under reduced pressure to yield a crude product which was recrystallized from methanol to yield the title compound, 0.28 g, m.p. 210–2° C.

EXAMPLE 52

7-(3-Methylsulphinylpropylamino)-4-oxo-2-(2-propoxyphenyl)-3,4-dihydropyrimido[4,5-d]pyrimidine A cool (0° C.) solution of 7-(3-methylthiopropylamino)-4-oxo-2-(2-propoxyphenyl)-3,4-dihydropyrimido[4,5-d]pyrimidine (1.84 g) and m-chloroperoxybenzoic acid (0.97 g) in dichloromethane (180 ml) was allowed to warm to ambient temperature with stirring. The solution was then stirred for 18 hours at ambient temperature and allowed to stand for 10 days. The reaction mixture was evaporated under reduced pressure and the residue eluted from a silica column with chloroform:methanol (gradient elution). The combined fractions containing product were evaporated under reduced pressure and the residue was recrystallized from isopropanol to yield the title compound, 1.73 g, m.p. 188–9° C.

EXAMPLE 53

7-(3-Methylsulphonylpropylamino)-4-oxo-2-(2-propoxyphenyl)-3,4-dihydropyrimido[4,5-d]pyrimidine A solution of 7-(3-methylsulphinylpropylamino)-4-oxo-2-(2-propoxyphenyl)-3,4,-dihydropyrimido[4,5-d]pyrimidine (0.80 g) and m-chloroperoxybenzoic acid (0.40 g) in dichloromethane (50 ml) was stirred at ambient temperature for 24 hours. During this time further m-chloroperoxybenzoic acid (about 200 mg) was added on 2 occasions. The solution was washed with dilute aqueous sodium bicarbonate (3×25 ml) and the combined washings back-extracted with a little dichloromethane. The combined organic layer was washed with water and then brine, dried (magnesium sulphate) and evaporated under reduced pressure to yield a residue. This was recrystallized three times from methanol to yield the title compound, 0.51 g, m.p. 222–3° C.

EXAMPLE 54

4,7-Dioxo-2-(2-propoxyphenyl)-3,4,7,8-tetrahydropyrimido[4,5-d]pyrimidine

7-Methylthio-4-oxo-2-(2-propoxyphenyl)-3,4-dihydropyrimido[4,5-d]pyrimidine (0.66 g) and methanol (0.26 g) were added to a stirring suspension of sodium hydride (0.38 g, 50% suspension in oil) in dry dimethylsulphoxide (15 ml). The mixture was stirred at ambient temperature for 1.5 hours and at 70–80° C. for 18 hours. The cooled reaction mixture was poured into water (500 ml), then glacial acetic acid (0.46 ml) was added and the mixture was extracted with chloroform (200 ml and then 2×100 ml). The combined extracts were washed with water, dried (magnesium sulphate) and evaporated under reduced pressure to yield a solid which was washed successively with ether and 40–60° petroleum ether and recrystallized from dimethylformamide:water to yield a crude product (0.18 g). This together with another sample (0.24 g) similarly prepared was eluted from a silica column with chloroform and 10% methanol in chloroform. The combined fractions containing product were evaporated under reduced pressure and the residue recrystallized from dimethylformamide:dilute hydrochloric acid and then from dimethylformamide to yield the title compound, 0.15 g, m.p. 271–3° C. (decomposition).

EXAMPLE 55

7-Methylsulphonyl-4-oxo-2-(2-propoxyphenyl)-3,4-dihydropyrimido[4,5-d]pyrimidine A solution of 7-methylthio-4-oxo-2-(2-propoxyphenyl)-3,4-dihydropyrimido[4,5-d]pyrimidine (3.0 g) and m-chloroperoxybenzoic acid (3.8 g) in dichloromethane (180 ml) was stirred at ambient temperature for 3 hours and then allowed to stand for 3 days. The solution was washed with dilute aqueous sodium bicarbonate (3×75 ml) and the combined washings extracted with dichloromethane (2×25 ml). The combined organic layers were washed successively with water and brine, dried (magnesium sulphate) and evaporated under reduced pressure to yield a crude product which was recrystallized from acetonitrile to yield the title compound, 2.04 g, m.p. 217–9° C.

EXAMPLE 56

7-Diethylamino-4-oxo-2-(2-propoxyphenyl)-3,4-dihydropyrimido[4,5-d]pyrimidine

A solution of 7-methylsulphonyl-4-oxo-2-(2-propoxyphenyl)-3,4-dihydropyrimido[4,5-d]pyrimidine (229 mg) and diethylamine (420 mg) in dichloromethane (8 ml) was stirred at ambient temperature for 3 hours. The reaction mixture was eluted from a silica column with diethyl ether:chloroform (4:1) and the combined fractions containing product were evaporated under reduced pressure to yield an oil which on trituration with 40–60° petroleum ether yielded the title compound, 85.5 mg, m.p. 116–7° C.

EXAMPLE 57

7-(2-Ethoxycarbonylethylamino)-4-oxo-2-(2-propoxyphenyl)-3,4-dihydropyrimido[4,5-d]pyrimidine A solution of 7-methylsulphonyl-4-oxo-2-(2-propoxyphenyl)-3,4-dihydropyrimido[4,5-d]pyrimidine (1.0 g), β-alanine ethyl ester hydrochloride (1.10 g) and triethylamine (0.73 g) in dichloromethane (20 ml) was stirred at ambient temperature for 2.5 hours. The reaction mixture was extracted with dilute hydrochloric acid (20 ml) then water (10 ml), and the extracts back washed with dichloromethane (10 ml). The combined organic extracts were dried (magnesium sulphate) and evaporated under reduced pressure to yield a crude product which was recrystallized from ethanol:water to yield the title compound, 0.83 g, m.p. 142–3° C.

EXAMPLE 58

7-(Ethoxycarbonylmethylamino)-4-oxo-2-(2-propoxyphenyl)-3,4-dihydropyrimido[4,5-d]pyrimidine In a similar manner to Example 57 reaction of 7-methylsulphonyl-4-oxo-2-(2-propoxyphenyl)-3,4-dihydropyrimido[4,5-d]pyrimidine (0.86 g), glycine ethyl ester hydrochloride (0.65 g) and triethylamine (0.47 g) in dichloromethane (15 ml) yielded the title compound, 0.38 g, m.p. 174.5–176° C. (recrystallized from ethanol:water).

EXAMPLE 59

7-(2-Carboxyethylamino)-4-oxo-2-(2-propoxyphenyl)-3,4-dihydropyrimido[4,5-d]pyrimidine A solution of 7-(2-ethoxycarbonylethylamino)-4-oxo-2-(2-propoxyphenyl)-3,4-dihydropyrimido[4,5-d]pyrimidine (0.53 g) in 1 Normal sodium hydroxide (5 ml) was stirred at ambient temperature for 2 hours. Acidification of the reaction mixture with concentrated hydrochloric acid yielded a precipitate which was recrystallized from ethanol:water to yield the title compound, 0.42 g, m.p. 227–8° C.

EXAMPLE 60

7-(Carboxymethylamino)-4-oxo-2-(2-propoxyphenyl)-3,4-dihydropyrimido[4,5-d]pyrimidine In a similar manner to Example 59 reaction of 7-(ethoxycarbonylmethylamino)4-oxo-2-(2-propoxyphenyl)-3,4-dihydropyrimido[4,5-d]pyrimidine (0.54 g) and 1 Normal sodium hydroxide (5 ml) yielded the title compound 0.41 g, m.p. 252–253.5° C. (dec.) (recrystallized from ethanol:water).

EXAMPLE 61

7-Ethoxy-4-oxo-2-(2-propoxyphenyl)-3,4-dihydropyrimido[4,5-d]pyrimidine

A solution of 7-methylsulphonyl-4-oxo-2-(2-propoxyphenyl)-3,4-dihydropyrimido[4,5-d]pyrimidine (0.50 g) in sodium ethoxide solution (from sodium, 0.16 g, and ethanol, 25 ml) was stirred at ambient temperature for 1.5 hours. Cooling and acidification of the reaction mixture with glacial acetic acid (0.42 g) yielded a precipitate which was twice recrystallized from ethanol to yield the title compound, 0.29 g, m.p. 196–197.5° C.

EXAMPLE 62

7-Methoxy-4-oxo-2-(2-propoxyphenyl)-3,4-dihydropyrimido[4,5-d]pyrimidine

In a similar manner to Example 61 reaction of 7-methylsulphonyl-4-oxo-2-(2-propoxyphenyl)-3,4-dihydropyrimido[4,5-d]pyrimidine (0.50 g) and sodium methoxide solution (from sodium, 0.16 g, and methanol, 20 ml) yielded the title compound, 0.29 g, m.p. 231–2° C. (recrystallized from methanol).

EXAMPLE 63

7-(2,2,2-Trifluoroethylamino)-4-oxo-2-(2-propoxylphenyl)-3 4-dihydropyrimido[4,5-d]pyrimidine A solution of 7-methylsulphonyl-4-oxo-2-(2-propoxyphenyl)-3,4-dihydropyrimido[4,5-d]pyrimidine (0.72 g), 2,2,2-trifluoroethylamine hydrochloride (0.97 g) and triethylamine (0.73 g) in dichloromethane (15 ml) was stirred at ambient temperature for 48 hours and allowed to stand for 4 days. A yellow solid had formed which was collected by filtration and washed with dichloromethane. The filtrate was washed with dilute hydrochloric acid (15 ml) then water (10 ml) and the aqueous layers extracted with dichloromethane (2×7.5 ml). The combined organic layers were dried (magnesium sulphate) and evaporated under reduced pressure to yield a crude product. This was eluted from a silica column with diethyl ether:chloroform (4:1) and the combined fractions containing product were evaporated under reduced pressure to yield a residue which was recrystallized from isopropanol to yield the title compound, 0.13 g, m.p. 214–215.5° C.

EXAMPLE 64

7-Propoxy-4-oxo-2-(2-propoxyphenyl)-3,4-dihydropyrimido[4,5-d]pyrimidine

In a similar manner to Example 63 reaction of 7-methylsulphonyl-4-oxo-2-(2-propoxyphenyl)-3,4-dihydropyrimido[4,5-d]pyrimidine (0.54 g) and sodium propoxide solution (from sodium, 0.17 g, and n-propanol, 25 ml) yielded the title compound, 0.19 g, m.p. 157–8° C. (recrystallized from n-propanol).

EXAMPLE 65

7-(N-Ethyl-N-hydroxyethylamino)-4-oxo-2-(2-propoxyphenyl)-3,4-dihydropyrimido[4,5-d]pyrimidine In a similar manner to Example 31 reaction of 7-methylsulphonyl-4-oxo-2-(2-propoxyphenyl)-3,4-dihydropyrimido[4,5-d]pyrimidine (0.40 g) and 2-(ethylamino)ethanol (0.64 g) in dichloromethane (12 ml) yielded the title compound, 137 mg, m.p. 141–2° C. (recrystallized from isopropanol-ether).

EXAMPLE 66

7-Dipropylamino-4-oxo-2-(2-propoxyphenyl)-3,4-dihydropyrimido[4,5-d]pyrimidine

In a similar manner to Example 56 reaction of 7-methylsulphonyl-4-oxo-2-(2-propoxyphenyl)-3,4-dihydropyrimido[4,5-d]pyrimidine (0.40 g) and dipropylamine (0.74 g) in dichloromethane (10 ml) yielded the title compound, 83 mg, m.p. 123–4° C. (recrystallized from cyclohexane).

EXAMPLE 67

7-(2-Phenethylamino)-4-oxo-2-(2-propoxyphenyl)-3,4-dihydropyrimido[4,5-d]pyrimidine In a similar manner to Example 56 reaction of 7-methylsulphonyl-4-oxo-2-(2-propoxyphenyl)-3,4-dihydropyrimido[4,5-d]pyrimidine (0.40 g) and phenethylamine yields the title compound.

EXAMPLE 68

2-(2-Propoxyphenyl)pyrido[2,3-d]pyrimid-4(3H)-one a) A solution of 2-propoxybenzoyl chloride (0.99 g) in acetonitrile (7.5 ml) was added dropwise over 5 minutes to a cooled (0° C.), stirred mixture of 2-aminonicotinamide (0.69 g) and triethylamine (0.51 g) in acetonitrile (7.5 ml). The reaction mixture was stirred at ambient temperature for 1.5 hours, allowed to stand overnight and then evaporated under reduced pressure to dryness. The residue was washed with water to afford a solid (1.63 g) which was twice recrystallized from methanol to afford 2-(2-propoxybenzamido)-nicotinamide, 0.92 g, m.p. 181–184° C.

b) A stirred mixture of 2-(2-propoxybenzamido)-nicotinamide (0.77 g) and pyridine (0.8 ml) in 2 Normal sodium hydroxide (20 ml) was heated under reflux for 30 minutes. The cooled reaction mixture was neutralized with 2 Normal hydrochloric acid to afford a precipitate which together with another precipitate similarly prepared from 2-(2-propoxybenzamido)nicotinamide (0.1 g) was recrystallized from ethanol-ether to afford white needles (0.65 g) which were washed with water to afford the title compound, 0.55 g, m.p. 110–111° C.

EXAMPLE 69

2-(2-Propoxyphenyl)pyrido[3,4-d]pyrimid-4(3H)-one a) In a similar manner to Example 68 a) reaction of 2-propoxybenzoyl chloride (0.99 g), 3-aminoisonicotinamide (0.69 g) and triethylamine (0.51 g) in acetonitrile (15 ml) afforded a crude product (1.45 g) which was recrystallized from methanol to afford 3-(2-propoxybenzamido)isonicotinamide, 0.73 g, m.p. 214–7° C.

b) In a similar manner to Example 68 b) cyclisation of 3-(2-propoxybenzamido)isonicotinamide (0.72 g) afforded a crude product which was recrystallized from ethanol-water to afford the title compound 0.44 g, m.p. 181–183° C.

EXAMPLE 70

2-(2-Propoxyphenyl)pyrido[4,3-d]pyrimid-4(3H)-one a) In a similar manner to Example 68 a) reaction of 2-propoxybenzoyl chloride (0.79 g), 4-aminonicotinamide (0.55 g) and triethylamine (0.40 g) in acetonitrile (12 ml) afforded a crude product which was recrystallized from ethanol-ether to afford 4-(2-propoxybenzamido) nicotinamide, 0.53 g, m.p. 164–166° C.

b) In a similar manner to Example 68 b) cyclisation of 4-(2-propoxybenzamido)nicotinamide (0.52 g) afforded a crude product which was recrystallized from ethanol-water to afford the title compound, 0.45 g, m.p. 135–136° C.

EXAMPLE 71

2-(2-Propoxyphenyl)pyrido[3,2-d]pyrimid-4(3H)-one a) In a similar manner to Example 68 a) reaction of 2-propoxybenzoyl chloride (0.99 g), 3-aminopicolinamide (0.69 g) and triethylamine (0.51 g) in acetonitrile (15 ml) afforded a crude product which was recrystallized from methanol to afford 3-(2-propoxybenzamido)picolinamide, 0.91 g, m.p. 116–118° C.

b) In a similar manner to Example 68 b) cyclisation of 3-(2-propoxybenzamido)picolinamide (0.90 g) afforded a crude product which was recrystallized from ethanol-water to afford the title compound, 0.28 g, m.p. 126–127° C.

The mother liquor was evaporated under reduced pressure to dryness and the residue recrystallized from ethanol-water to afford a further sample of the title compound, 0.46 g, m.p. 125–126.5° C.

EXAMPLE 72

2-(2-Propoxyphenyl)pteridin-4(3H)-one

A stirred mixture of 4,5-diamino-2-(2-propoxyphenyl) pyrimidin-6-one sulphate (1.25 g), glyoxal hydrate (0.4 g), water (62.5 ml) and n-butanol (1 ml) was heated under reflux for one hour to afford a crude product (0.97 g) which was collected and washed with water. The crude product together with another sample (0.12 g) similarly prepared was eluted from a silica column with chloroform. The combined fractions containing product were evaporated under reduced pressure to afford a solid (0.96 g) which was recrystallized from ethanol-water to afford the title compound, 0.8 g, m.p. 177.5–178.5° C.

EXAMPLE 73

2-(2-Propoxyphenyl)pteridin-4,6(3H,5H)-dione

A solution of chloral hydrate (1.74 g) in 50% aqueous methanal (10 ml) was added over 10 minutes to a stirred solution of 4,5-diamino-2-(2-propoxyphenyl)pyrimidin-6-one sulphate (1.89 g) in 50% aqueous methanol (60 ml) at 80° C. and the reaction mixture was stirred at 80° C. for 1.5 hours. The cooled reaction mixture was filtered to remove an orange brown solid which was discarded. On standing overnight the filtrate afforded a crude solid product (0.96 g) which was collected and washed with dilute aqueous potassium bicarbonate and water. The crude product together with another sample (0.20 g) similarly prepared was eluted from a silica column with chloroform. The combined fractions containing product were evaporated under reduced pressure to afford a solid (0.54 g) which was recrystallized from acetonitrile to afford the title compound, 0.39 g, m.p. 232–233.5° C.

EXAMPLE 74

2-(2-Propoxyphenyl)pteridin-4,6,7(3H,5H,8H)-trione

A stirred mixture of 4,5-diamino-2-(2-propoxyphenyl) pyrimidin-6-one sulphate (1.0 g), triethylamine (0.42 ml) and diethyl oxalate (1.2 ml) in methoxyethanol (10 ml) was heated under reflux for 7 hours. The reaction mixture was stirred overnight at ambient temperature and a precipitate was collected and washed with water and ethanol to afford a crude product (0.70 g, m.p. 312–315° C.). The crude product together with another sample (0.34 g) similarly prepared was twice recrystallized from dimethylformamide to afford the title compound, 0.40 g, m.p. 320–321° C.

EXAMPLE 75

5,6-Dihydro-3-methylthio-5-oxo-7-(2-propoxyphenyl)pyrimido[5,4-e][1,2,4]triazine a) A filtered solution of 2-propoxybenzamidine in ethanol (prepared from sodium, 0.28 g, in ethanol, 50 ml, and 2-propoxybenzamidine hydrochloride, 2.63 g) was added to a stirred, cooled solution of ethyl 3-chloro-6-methylthio-1, 2,4-triazine-5-carboxylate (2.6 g) in ethanol (50 ml). After one hour the temperature was allowed to rise to ambient, stirred for a further one hour, then filtered to give 6-chloro-3-methylthio-5-(2-propoxybenzamidinocarbonyl)-1,2,4-triazine, 3.45 g, m.p. 229–230° C.

b) A stirred mixture of the product from (a) above (3.45 g), potassium carbonate (1.3 g) and dimethylformamide (200 ml) was heated at 150° C. for 6.5 hours. Potassium carbonate (1.3 g) was added and the mixture was heated for a further 2 hours. Water (150 ml) was added to the residue left after evaporation, and the mixture was acidified with acetic acid to give 5,6-dihydro-3-methylthio-5-oxo-7-(2-propoxyphenyl)pyrimido[5,4-e][1,2,4]triazine 2.88 g, m.p. 195–197° C. Recrystallization from ethanol gave the pure product m.p. 224–225° C.

EXAMPLE 76

3-Amino-5,6-dihydro-5-oxo-7-(2-propoxyphenyl)
pyrimido[5,4-e][1,2,4]triazine 5,6-Dihydro-3-methylthio-5-oxo-7-(2-propoxyphenyl) pyrimido[5,4-e][1,2,4]triazine (0.7 g) was heated for 30 hours with ethanolic ammonia (50 ml) at 100° C. in a pressure vessel. The cooled mixture was filtered to give the crude product (0.21 g) which was recrystallized from ethanol to give the pure title compound, m.p. 322–325° C.

EXAMPLE 77

3-Methylamino-5,6-dihydro-5-oxo-7-(2-propoxyphenyl)pyrimido[5,4-e][1,2,4]triazine 5,6-Dihydro-3-methylthio-5-oxo-7-(2-propoxyphenyl) pyrimido[5,4-e][1,2,4]triazine (340 mg) was treated with a solution of methylamine in industrial methylated spirit (33%, 15 ml) at 70° C. in a pressure vessel (172 kPa) for 10 hours. The cooled reaction mixture was evaporated under reduced pressure to afford a yellow solid (290 mg) which was recrystallized from ethanol and then acetonitrile to afford the title compound, 120 mg, m.p. decomposes over 260° C.

EXAMPLE 78

3-Methoxy-5,6-dihydro-5-oxo-7-(2-propoxyphenyl)
pyrimido[5,4-e][1,2,4]triazine

A stirred mixture of 5,6-dihydro-3-methylthio-5-oxo-7-(2-propoxyphenyl)pyrimido[5,4-e][1,2,4]triazine (0.80 g) and sodium methoxide (prepared from sodium, 0.28 g and methanol) in methanol (50 ml) was heated under reflux for 1.5 hours. The cooled reaction mixture was neutralized by the addition of glacial acetic acid (0.7 ml) to afford a yellow precipitate (0.63 g) which was recrystallized from methanol to afford the title compound, 0.47 g, m.p. 221–222° C.

EXAMPLE 79

3-Methylthio-8-oxo-6-(2-propoxyphenyl)-7,8-
dihydropyrimido[4,5-e][1,2,4]triazine A solution of 2-propoxybenzamidine (from 2.9 g of the hydrochloride) in 2-propanol (50 ml) was added at 2° C. to a solution of 3-methylthio-5-chloro-8-carboethoxy-1,2,4-triazine (2.08 g) in 2-propanol (100 ml). The mixture was stirred at 2° C. for 2 hours, allowed to stand at room temperature overnight, and then heated under reflux for 3 hours. The residue left after evaporation was dissolved in chloroform and the solution was washed with dilute hydrochloric acid. Evaporation of the chloroform and treatment of the residue with ethanol gave a solid (0.2 g) which was recrystallized from ethanol to give 3-methylthio-8-oxo-6-(2-propoxyphenyl)-7,8-dihydropyrimido[4,5-e][1,2,4] triazine, 0.12 g, m.p. 247–249° C.

EXAMPLE 80

3-Amino-8-oxo-6-(2-propoxyphenyl)-7,8-
dihydropyrimido[4,5-e][1,2,4]triazine

In a similar manner to that described in Example 87, 3-methylthio-8-oxo-6-(2-propoxyphenyl)-7,8-dihydropyrimido[4,5-e][1,2,4]triazine (1.42 g) was reacted with ethanolic ammonia (70 ml) for 20 hours to give the crude title compound, (0.80 g) which together with another sample (0.17 g), similarly prepared, was recrystallized from ethanol to afford the title compound, 0.54 g, m.p. 255–256° C.

EXAMPLE 81

3-Methylamino-8-oxo-6-(2-propoxyphenyl)-7,8-
dihydropyrimido[4,5-e][1,2,4]triazine 3-Methylthio-8-oxo-6-(2-propoxyphenyl)-7,8-dihydropyrimido[4,5-e][1,2,4]triazine (2.0 g) was treated with a solution of methylamine in industrial methylated spirit (33%, 30 ml) at 75° C. in a pressure vessel for 20 hours. The cooled reaction mixture was evaporated under reduced pressure to afford an oily solid which was dissolved in chloroform. The organic solution was washed with water, dried and evaporated under reduced pressure to afford a yellow oily solid which was eluted from a silica column with chloroform/methanol (5%). The fractions containing product were combined and evaporated under reduced pressure to afford a yellow solid (180 mg) which together with another sample (50 mg), similarly prepared, was recrystallized from ethanol to afford the title compound, 140 mg, m.p. 261–263° C.

EXAMPLE 82

3-Methoxy-8-oxo-6-(2-propoxyphenyl)-7,8-
dihydropyrimido[4,5-e][1,2,4]triazine

In a similar manner to Example 78, 3-methylthio-8-oxo-6-(2-propoxyphenyl)-7,8-dihydropyrimido[4,5-e][1,2,4] triazine (0.5 g) was treated for 3 hours with sodium methoxide (prepared from sodium, 0.17 g, and methanol) to afford the title compound, 0.34 g, m.p. 234–235° C. (recrystallized from methanol).

EXAMPLE 83

3,8-Dioxo-6-(2-propoxyphenyl) 3,4,7,8-
tetrahydropyrimido[4,5-e][1,2,4]triazine

A stirred mixture of 3-methylthio-8-oxo-6-(2-propoxyphenyl)-7,8-dihydropyrimido[4,5-e][1,2,4]triazine (0.5 g) and sodium methoxide (prepared from sodium, 0.17 g. and methanol) in methanol (50 ml) was heated under reflux for 3 hours. The cooled reaction mixture was evaporated under reduced pressure to afford a yellow solid which was dissolved in water and acidified with 2 Normal hydrochloric acid to yield a yellow solid (420 mg) which was recrystallized from dimethylformamide to afford the title compound, 0.16 g, m.p. 296–299° C.

EXAMPLE 84

3-Dimethylamino-8-oxo-6-(2-propoxyphenyl)-7,8-
dihydropyrimido[4,5-e][1,2,4]triazine 3-Methylthio-8-oxo-6-(2-propoxyphenyl)-7,8-dihydropyrimido[4,5-e][1,2,4]triazine (0.6 g) was treated with a solution of dimethylamine in industrial methylated spirit (33%, 20 ml) at 100° C. in a pressure vessel for 24 hours. The cooled reaction mixture was evaporated under reduced pressure to afford a yellow solid residue which was dissolved in dilute aqueous sodium hydroxide and filtered. The filtrate was acidified with a few drops of concentrated hydrochloric acid to afford a yellow precipitate which was collected, washed from water and recrystallized from methanol to afford the title compound, 0.44 g, m.p. 257.5–259° C.

EXAMPLE 85

3-Methylthio-8-oxo-6-(2-allyloxyphenyl)-7,8-
dihydropyrimido[4,5-e][1,2,4]triazine A cooled (5° C.) solution of 3-methylthio-5-chloro-6-carboethoxy-1,2,4-triazine prepared by heating 3-methylthio-5-oxo-6-carboethoxy-4,5-dihydro-1,2,4-triazine, 1.5 g with thionyl chloride, 30 ml, under reflux for two hours and thereafter removing thionyl chloride) in acetonitrile (30 ml) was added to a cooled stirred mixture of 2-allyloxybenzamidine hydrochloride (2.23 g) and triethylamine (1.06 g) in acetonitrile (50 ml). The mixture was stirred with cooling (0–5° C.) for 15 minutes, then more triethylamine (0.71 g) was added and the reaction mixture was stirred at ambient temperature for two hours and left standing overnight. A yellow precipitate was collected, washed with water and recrystallized from acetonitrile and then from acetonitrile-ethanol (50%) to afford the title compound, 0.35 g, m.p. 238–239° C.

EXAMPLE 86

3-Methylthio-8-oxo-6-(2-isobutoxyphenyl)-7,8-dihydropyrimido[4,5-e][1,2,4]triazine In a similar manner to Example 85 reaction of 3-methylthio-5-chloro-6-carboethoxy-1,2,4-triazine (prepared from 3-methylthio-5-oxo-6-carboethoxy-4,5-dihydro-1,2,4-triazine, 1.5 g) with 2-isobutoxybenzamidine hydrochloride (2.37 g) and triethylamine (1.75 g) afforded the crude title compound (1.71 g). This was recrystallized from acetonitrile, then dissolved in chloroform, the organic solution was washed with 2 Normal hydrochloric acid (×2), chloroform removed under reduced pressure and the residue recrystallized twice from ethanol to afford the title compound, 0.32 g, m.p. 237–238° C.

EXAMPLE 87

3-Methylthio-8-oxo-6-(2-cyclopropylmethoxyphenyl)-7,8-dihydropyrimido[4,5-e][1,2,4]triazine In a similar manner to Example 85 reaction of 3-methylthio-5-chloro-6-carboethoxy-1,2,4-triazine (prepared from 3-methylthio-5-oxo-6-carboethoxy-4,5-dihydro-1,2,4-triazine, 1.5 g) with 2-cyclopropoxybenzamidine hydrochloride (2.35 g) and triethylamine (1.75 g) afforded a yellow solid (1.31 g) which was recrystallized from acetonitrile and then from acetonitrile/ethanol (50%) to afford the title compound, 0.70 g, m.p. 235–236° C.

EXAMPLE 88

3-Methylthio-8-oxo-6-(2-methoxyphenyl)-7,8-dihydropyrimido[4,5-e][1,2,4]triazine A cooled (0° C.) solution of 2-methoxybenzamidine (from 1.97 g of the hydrochloride) in acetonitrile (17 ml) was added to a cooled solution of 3-methylthio-5-chloro-6-carboethoxy-1,2,4-triazine (prepared from 3-methylthio-5-oxo-6-carboethoxy-4,5-dihydro-1,2,4-triazine, 1.08 g, and thionyl chloride, 20 ml) in acetonitrile (17 ml). Triethylamine (0.51 g) was added and the reaction mixture was stirred with cooling (0° C.) for one hour and then at ambient temperature for 17 hours to afford a yellow solid which was washed with acetonitrile and ether to afford the crude title compound (1.39 g). A sample (0.35 g) of this was washed twice with boiling methanol to afford the title compound, 0.25 g, m.p. 267.5–268.5° C. The remaining material (1.04 g) was similarly treated with boiling methanol to afford the title compound, 0.91 g, m.p. 266–268° C.

EXAMPLE 89

Pharmaceutical compositions for oral administration are prepared by combining the following:

| | % W/W | | |
|---|---|---|---|
| 2-(2-Propoxyphenyl)pyrido-[2,3-d]pyrimid-4(3H)-one | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

EXAMPLE 90

A pharmaceutical composition for parenteral administration is prepared by dissolving the title compound of Example 9 (0.02 g) in polyethylene glycol 300 (25 ml) with heating. This solution is then diluted with water for injections Ph. Eur. (to 100 ml). The solution is then sterilized by filtration through a 0.22 micron membrane filter and sealed in sterile containers.

Preparation 1

Diethyl 4-n-propylpyridine-2,3-dicarboxylate

A solution of diethyl 3-chloro-2-oxosuccinate (137.4 g, 0.69 mol), hexen-2-al (72.5 g, 0.74 mol) and ammonium sulphamate (190.2 g, 1.66 mol) in ethanol (450 ml) was stirred under reflux for 36 hours and then filtered. The filtrate was evaporated under vacuum, the resulting residue dissolved in water (500 ml) and this solution extracted with ethyl acetate (6×500 ml). The combined organic extracts were dried (MgSO$_4$) and evaporated under vacuum, then the resulting residue was chromatographed on silica gel (50 g), using an ethyl acetate in hexane elution gradient (0–20% ethyl acetate), to give the title compound as an orange oil (34.1 g, 21%). Rf 0.20 (ethyl acetate:hexane, 20:80).

Preperation 2

4-n-Propylpyridine-2,3-dicarboxamide

A mixture of liquid ammonia (40 ml) and diethyl 4-n-propylpyridine-2,3-dicarboxylate (Preparation 1; 2.0 g, 0.0075 mol) was heated in an autoclave at 100° C. for 18 hours and then allowed to cool. The ammonia was allowed to evaporate, then the residue was azeotroped with methanol and crystallized from ethyl acetate:methanol to give the title compound as a colourless solid (0.1 g, 6.4%), m.p. 178–179° C.

Preperation 3

7-n-Propyl-4-azaphthalimide

A stirred solution of 4-n-propylpyridine-2,3-dicarboxamide (Preparation 2; 0.1 g, 0.00048 mol) in N,N-dimethylacetamide (10 ml) was heated at 160° C. for 5 hours and then the solvent was evaporated under vacuum. The residue was purified by chromatography on silica gel (5 g), eluting with a solution of 3% methanol in dichloromethane, followed by crystallization from ethyl acetate to give the title compound as a light yellow solid (0.014 g, 15%), m.p. 163–165° C.

Preparation 4

3-Amino-4-n-propylpyridine-2-carboxylic acid

A stirred solution of 7-n-propyl-4-azaphthalimide (Preparation 3; 1.9 g, 0.010 mol) in aqueous sodium hydroxide solution (2.8 g, 0.07 mol of NaOH in 30 ml of water) was treated with aqueous sodium hypochlorite solution (5 ml, 0.010 mol). The resulting mixture was heated at 80° C. for 0.5 hour, cooled and acidified with dilute sulphuric acid (50%, 2 ml). The suspension produced was filtered and the solid thus obtained was crystallized from water to give the title compound as an off-white solid (0.33 g, 21%), m.p. 185–188° C.

Preparation 5

Ethyl 3-amino-4-n-propylpyridine-2-carboxylate

3-Amino-4-n-propylpyridine-2-carboxylic acid (Preparation 4; 0.36 g, 0.002 mol) was added to a stirred mixture of cesium carbonate (0.325 g, 0.001 mol) in water (20 ml), then this mixture was evaporated under vacuum and the residue azeotroped with dimethylformamide (2×20 ml). The resulting cesium salt was suspended in dimethylformamide (3 ml) and the stirred suspension then treated dropwise with ethyl iodide (0.17 ml, 0.0021 mol). After a further 0.25 hour, the solvent was evaporated under vacuum and the residue partitioned between water (20 ml) and ethyl acetate (20 ml). The organic phase was washed with water (10 ml), dried ($MgSO_4$) and evaporated under vacuum, then the residue crystallized from acetone:hexane to give the title compound as an off-white solid (0.35 g, 84%), m.p. 93–96° C.

Preparation 6

3-Amino-4-n-propylpyridine-2-carboxamide

A mixture of ethyl 3-amino-4-n-propylpyridine-2-carboxylate (Preparation 5; 7.4 g, 0.035 mol) and liquid ammonia (60 ml) was heated in an autoclave at 100° C. for 18 hours. The mixture was allowed to cool and the ammonia to evaporate, then the residue was crystallized from methanol to give the title compound as a colourless solid (4.84 g, 76%), m.p. 139–141° C.

Preparation 7

3-(2-Ethoxybenzoylamino)-4-n-propylpyridine-2-carboxamide

2-Ethoxybenzoyl chloride (2.96 g, 0.016 mol) was added dropwise to a stirred solution of 3-amino-4-n-propylpyridine-2-carboxamide (Preparation 6; 1.43 g, 0.008 mol) in pyridine (40 ml) at 0° C. The mixture was stirred at ambient temperature for 4 hours and then the solvent evaporated under vacuum. The residue was dissolved in dichloromethane (100 ml), the solution washed with saturated aqueous sodium carbonate solution (100 ml) and the aqueous phase then washed with dichloromethane (2×25 ml). The combined organic extracts were dried ($MgSO_4$) and evaporated under vacuum, then the residue purified by chromatography on silica gel (15 g), using a methanol in dichloromethane elution gradient (0–3% methanol), followed by crystallization from ethyl acetate to give the product as a light brown solid (1.36 g, 60%), 129–131° C.

Preparation 8

2-(2-Ethoxyphenyl)-8-n-propylpyrido[3,2-d]pyrimidin-4(3H)-one

A mixture of 3-(2-ethoxybenzoylamino)-4-n-propylpyridine-2-carboxamide (Preparation 7; 1.52 g, 0.0046 mol) and anhydrous zinc chloride (1.88 g, 0.014 mol) was heated at 210° C. for 0.25 hour. The cool mixture was dissolved in methanol (20 ml) and this solution poured into an aqueous solution of disodium ethylenediamine tetraacetic acid (10.3 g in 200 ml water). The resulting mixture was basified with saturated aqueous sodium carbonate solution (20 ml), then extracted with dichloromethane (4×60 ml). The combined organic extracts were dried ($MgSO_4$) and evaporated under vacuum, then the residue crystallized from ethyl acetate to give the title compound as a white solid (0.92 g, 65%), m.p. 134–137° C.

Preparation 9

3-(2-Ethoxybenzoylamino)pyridine-2-carboxamide

The title compound was prepared from 2-ethoxybenzoyl chloride and 3-aminopyridine-2-carboxamide (J. Chem. Soc., 1956, 1045) following the procedure of Preparation 7 and was obtained as an off-white solid (100%), m.p. 172–177° C.

Preparation 10

2-(2-Ethoxyphenyl)pyrido[3,2-d]pyrimidin-4 (3H)-one

The title compound was prepared from 3-(2-ethoxybenzoylamino)pyridine-2-carboxamide (Preparation 9) following the procedure of Preparation 8 and was obtained as an off-white solid (56%), m.p. 184–187° C.

Preparation 11

Ethyl 3-amino-4-cyanopyridine-2-carboxylate

A stirred solution of ethyl 2-cyano-2-(formylamino)acetate (J. Org. Chem., 1979, 44, 3835; 0.47 g, 0.003 mol), acrylonitrile (1.2 ml, 0.018 mol) and tri-fluoroacetic acid (0.02 ml, 0.0003 mol) in 1,2-dichloroethane (4 ml) was heated under reflux for 3 days. The solvent was removed by evaporation under vacuum, the residue dissolved in dichloromethane (30 ml) and the resulting solution washed with saturated aqueous sodium bicarbonate solution (30 ml). The aqueous phase was washed with dichloromethane (30 ml) and the organic solutions then combined, dried ($MgSO_4$) and evaporated under vacuum. Chromatography of the residue on silica gel (12 g), eluting with dichloromethane:methanol (100:1), followed by crystallization from acetone:hexane, gave the title compound as a colourless solid (0.12 g, 21%), m.p. 114–116° C.

Preparation 12

3-Amino-4-cyanopyridine-2-carboxamide

A mixture of liquid ammonia (30 ml) and ethyl 3-amino-4-cyanopyridine-2-carboxylate (Preparation 11; 2.8 g, 0.0147 mol) was heated at 100° C. in an autoclave for 18 hours. The ammonia was allowed to evaporate and the resulting product crystallized from ethyl acetate to give the title compound as an off-white solid (2.2 g, 94%), m.p. >310° C.

Preparation 13

4-Cyano-3-(2-ethoxybenzoylamino)pyridine-2-carboxamide

The title compound was prepared from 2-ethoxybenzoyl chloride and 3-amino-4-cyanopyridine-2-carboxamide (Preparation 12), following the procedure of Preparation 7, and was obtained as a colourless solid (6.2%), m.p. 150–152° C.

Preparation 14

8-Cyano-2-(2-ethoxyphenyl)pyrido[3,2-d]pyrimidin-4(3H)-one

The title compound was prepared from 4-cyano-3-(2-ethoxybenzoylamino)pyridine-2-carboxamide (Preparation 13), following the procedure of Preparation 9, and was obtained as a white solid (54%), m.p. 255–256° C.

Preparation 15

8-Carbamoyl-2-(2-ethoxyphenyl)pyrido[3,2-d]pyrimidin-4(3H)-one

30% Aqueous hydrogen peroxide solution (0.5 ml) was added to a stirred aqueous sodium hydroxide solution (1M, 40 ml), followed by 8-cyano-2-(2-ethoxyphenyl)pyrido[3,2-d]pyrimidin-4(3H)-one (Preparation 14; 0.2 g, 0.00068 mol) and ethanol (2 ml). The mixture was heated under reflux for 2 hours, allowed to cool, acidified with 1N hydrochloric acid, and then extracted with a mixture of dichloromethane and methanol (10:1, 5×50 ml). The combined organic fractions were evaporated under vacuum and the resulting residue triturated with ethanol to give the title compound as a colourless solid (0.152 g, 72%), m.p. 295–297° C.

It will be understood that various changes and modifications can be made in the details of procedure, formulation and use without departing from the spirit of the invention, especially as defined in the following claims.

We claim:

1. A method for regulating apoptosis in autoimmune diseases in human cells, comprising exposing said cells to an effective amount of a compound of the formula:

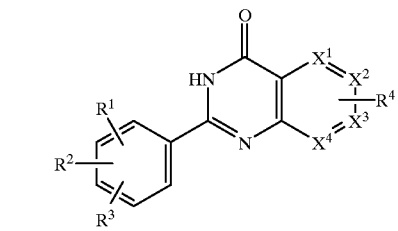

(I)

wherein $R^1$, $R^2$ and $R^3$ may be located at any of the available positions on the phenyl ring, each of $R^1$, $R^2$ and $R^3$ may be independently selected from hydrogen, halogen, a lower alkyl group, such as having 1 to 6 carbon atoms, a lower alkoxy, a lower alkenyl, a lower alkenoxy, a lower alkyl thio, a lower alkylamino, a di(lower)alkylamino, a cyano, an acylamino, a carboxyl, a carboalkoxy, a lower alkoxycarbonyl, a lower alkylcarbonyl, a cyclo(lower) alkoxy and cyclo (lower) alkyl (lower)alkyloxy in which the ring contains 3 to 8 carbon atoms, preferably 3–6 carbon atoms, a phenyl(lower) alkoxy, a nitrogen containing ring, a lower alkylcarbamoyloxy, or a halogen substituted lower alkyloxy group;

$R^4$ may be a lower alkyl, a lower alkoxy, a phenyl, a hydroxy, a halogen, —NHCOR$^5$, —NHCONHR$^6$, 5-tetrazolyl, —CO$_2$R$^7$, a cyano, —CONR$^8$R$^9$, or —NR$^{10}$R$^{11}$, wherein R$^5$ to R$^9$ are independently hydrogen or lower alkyl or R$^9$ may be 5-tetrazolyl, and R$^{10}$ and R$^{11}$ are independently hydrogen or lower alkyl optionally substituted by hydroxy provided that the carbon atom adjacent to the nitrogen atom is not substituted by hydroxy; and $X^1$, $X^2$, $X^3$ and $X^4$ may be independently nitrogen or carbon with the proviso that: at least one of $X^1$, $X^2$, $X^3$ and $X^4$ must be nitrogen and at least one of $X^1$, $X^2$, $X^3$ and $X^4$ must be carbon; any two of $X^1$, $X^2$, $X^3$ and $X^4$ may be nitrogen; when $X^2$ and $X^4$ are nitrogen, $X^3$ must be carbon; and, when $X^1$ and $X^3$ are nitrogen, $X^2$ must be carbon.

2. The method of claim 1 wherein $R^1$, $R^2$ and $R^3$ are independently a hydrogen, a halogen, a lower alkyl, a lower alkenyl, a lower alkoxy, a lower alkenyloxy, a phenyl(lower) alkoxy, a cyclo(lower)alkoxy.

3. The method of claim 2 wherein $R^1$ and $R^2$ are hydrogen, and $R^3$ is lower alkoxy, lower alkenoxy, cyclopropylmethoxy or benzoxy.

4. The method of claim 1 wherein $R^4$ is a phenyl, a lower alkyl, a hydroxy, a lower alkoxy or a —CONR$^8$R$^9$.

* * * * *